US010624584B2

(12) United States Patent
Samuelsson

(10) Patent No.: US 10,624,584 B2
(45) Date of Patent: *Apr. 21, 2020

(54) INTERFACE UNIT, MEASUREMENT SYSTEM AND A METHOD IN AN INTERFACE UNIT

(75) Inventor: Magnus Samuelsson, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 1316 days.

This patent is subject to a terminal disclaimer.

(21) Appl. No.: 13/884,471

(22) PCT Filed: Nov. 9, 2011

(86) PCT No.: PCT/EP2011/069728
§ 371 (c)(1),
(2), (4) Date: May 9, 2013

(87) PCT Pub. No.: WO2012/062797
PCT Pub. Date: May 18, 2012

(65) Prior Publication Data
US 2013/0225941 A1 Aug. 29, 2013

Related U.S. Application Data

(60) Provisional application No. 61/413,012, filed on Nov. 12, 2010, provisional application No. 61/446,568, filed on Feb. 25, 2011.

(30) Foreign Application Priority Data

Feb. 25, 2011 (SE) ........................................ 1150174

(51) Int. Cl.
*A61B 5/00* (2006.01)
*A61B 5/01* (2006.01)
(Continued)

(52) U.S. Cl.
CPC .......... *A61B 5/6876* (2013.01); *A61B 5/0002* (2013.01); *A61B 5/01* (2013.01);
(Continued)

(58) Field of Classification Search
CPC ...... A61N 1/00; A61B 5/6876; A61B 5/6851; A61B 5/7225; A61B 18/00; A61B 2560/045
See application file for complete search history.

(56) References Cited

U.S. PATENT DOCUMENTS 4,288,854 A    9/1981  Burroughs
4,911,167 A *  3/1990  Corenman ......... A61B 5/02416
                                              600/324
(Continued)

FOREIGN PATENT DOCUMENTS

EP    1 055 392 B1    3/2008
JP    06-186103 A     7/1994
(Continued)

OTHER PUBLICATIONS

Samuelsson, U.S. Non-Final Office Action, U.S. Appl. No. 14/000,750, dated Dec. 3, 2015, (16 pgs.).
(Continued)

*Primary Examiner* — Timothy J Neal
*Assistant Examiner* — Jae Woo
(74) *Attorney, Agent, or Firm* — Foley & Lardner LLP

(57) ABSTRACT

The present invention relates to an extracorporeale interface unit (8), for an intravascular measurement system for measuring a physiological, or other, variable in a living body, being adapted to generate a sensor signal in response of said variable. The interface unit (8) comprises a sensor interface circuitry (6) adapted to interface a sensor wire configured to be inserted into the living body and provided with one or many sensor element(s) at its distal region. The sensor
(Continued)

interface circuitry (6) further comprises a measurement unit (9) adapted to generate the measured data of the variable as a sensor signal. The sensor interface circuitry (6) comprises two current source units (CSU1, CSU2) adapted to energize the sensor element(s) via at least two connection points (CP1, CP2, . . . CPn), and a switching unit (10), wherein the switching unit (10) is adapted to alternately switch connection between the current source units (CSU1, CSU2) and at least two of the connection points (CP1, CP2, . . . CPn), using a preset switching frequency having essentially the same connection time period ($T_c$) for each connection. The measurement unit (9) is adapted to determine a sensor variable value ($V_{diff}$) related to the variable at two of the connection points (CP1, CP2, . . . CPn). The present invention further relates to a measurement system (12) comprising said extracorporeale interface unit (8) and a method in said interface unit.

27 Claims, 6 Drawing Sheets

(51) Int. Cl.
| | | |
|---|---|---|
| *A61N 1/00* | (2006.01) | |
| *A61B 5/026* | (2006.01) | |
| *A61B 5/0215* | (2006.01) | |
| *A61B 18/00* | (2006.01) | |
| *A61B 18/12* | (2006.01) | |
| *A61N 1/36* | (2006.01) | |
| *A61B 5/02* | (2006.01) | |

(52) U.S. Cl.
CPC .......... *A61B 5/0215* (2013.01); *A61B 5/4836* (2013.01); *A61B 5/6851* (2013.01); *A61B 5/7203* (2013.01); *A61B 5/7217* (2013.01); *A61B 5/7225* (2013.01); *A61B 18/00* (2013.01); *A61B 18/12* (2013.01); *A61N 1/00* (2013.01); *A61N 1/36* (2013.01); *A61B 5/02* (2013.01); *A61B 5/026* (2013.01); *A61B 2018/00577* (2013.01); *A61B 2018/00642* (2013.01); *A61B 2018/00708* (2013.01); *A61B 2018/00791* (2013.01); *A61B 2560/0252* (2013.01); *A61B 2560/045* (2013.01); *A61B 2562/227* (2013.01)

(56) References Cited

U.S. PATENT DOCUMENTS

| | | | | |
|---|---|---|---|---|
| 4,915,113 A * | 4/1990 | Holman | ............... | A61B 5/6876 600/504 |
| 5,117,113 A | 5/1992 | Thomson et al. | | |
| 5,357,956 A | 10/1994 | Nardella | | |
| 5,515,295 A | 5/1996 | Wang | | |
| 5,544,651 A * | 8/1996 | Wilk | ............... | A61B 5/14532 600/310 |
| 5,568,815 A | 10/1996 | Raynes et al. | | |
| 5,668,320 A | 9/1997 | Cowan et al. | | |
| 5,967,986 A * | 10/1999 | Cimochowski | ...... | A61B 5/0031 600/454 |
| 6,112,598 A | 9/2000 | Tenerz et al. | | |
| 6,171,252 B1 * | 1/2001 | Roberts | ............... | A61B 5/0215 324/678 |
| 6,248,083 B1 * | 6/2001 | Smith | ............... | A61B 5/0215 600/561 |
| 6,409,677 B1 * | 6/2002 | Tulkki | ............... | A61B 5/01 600/549 |
| 6,565,514 B2 * | 5/2003 | Svanerudh | ............... | A61B 5/6851 600/485 |
| 6,586,943 B1 * | 7/2003 | Masuda | ............... | G01D 3/032 324/500 |
| 6,712,772 B2 * | 3/2004 | Cohen | ............... | A61B 5/0215 600/485 |
| 7,207,227 B2 | 4/2007 | Rangsten et al. | | |
| 7,413,547 B1 * | 8/2008 | Lichtscheidl | ........ | A61B 5/0215 600/485 |
| 7,724,148 B2 | 5/2010 | Samuelsson et al. | | |
| 2002/0059827 A1 * | 5/2002 | Smith | ............... | A61B 5/0215 73/204.26 |
| 2002/0134163 A1 | 9/2002 | Clifford | | |
| 2002/0173724 A1 * | 11/2002 | Dorando | ............. | A61B 5/0215 600/486 |
| 2003/0125790 A1 * | 7/2003 | Fastovsky | ............ | A61B 5/0215 623/1.11 |
| 2003/0163052 A1 | 8/2003 | Mott et al. | | |
| 2004/0012379 A1 | 1/2004 | Van Deursen et al. | | |
| 2004/0225184 A1 | 11/2004 | Shimizu et al. | | |
| 2006/0009817 A1 * | 1/2006 | Tulkki | ............... | A61B 5/0002 607/60 |
| 2006/0207335 A1 * | 9/2006 | Tenerz | ................ | A61B 5/0215 73/754 |
| 2007/0043298 A1 | 2/2007 | Plouf et al. | | |
| 2007/0106165 A1 * | 5/2007 | Tulkki | ............... | A61B 5/0215 600/486 |
| 2007/0142727 A1 * | 6/2007 | Zhang | ................ | A61B 5/0031 600/486 |
| 2007/0255144 A1 | 11/2007 | Tulkki et al. | | |
| 2008/0033254 A1 * | 2/2008 | Kamath | ............. | A61B 5/14532 600/300 |
| 2008/0200770 A1 * | 8/2008 | Hubinette | ............ | A61B 5/0215 600/300 |
| 2009/0124880 A1 | 5/2009 | Smith | | |
| 2009/0299157 A1 * | 12/2009 | Telfort | ............... | A61B 5/14551 600/301 |
| 2010/0268038 A1 | 10/2010 | Smith | | |
| 2010/0331916 A1 | 12/2010 | Parramon et al. | | |
| 2012/0271178 A1 * | 10/2012 | Smith | ................... | A61B 5/6851 600/486 |
| 2013/0324806 A1 | 12/2013 | Samuelsson | | |
| 2015/0313478 A1 * | 11/2015 | Veszelei | ............... | A61B 5/0215 600/483 |

FOREIGN PATENT DOCUMENTS

| | | | |
|---|---|---|---|
| JP | 10-505269 | A | 5/1998 |
| JP | 10-267779 | A | 10/1998 |
| JP | 2000-504249 | A | 4/2000 |
| JP | 2001-33330 | A | 2/2001 |
| JP | 2007-000244 | A | 1/2007 |
| JP | 2009-504357 | A | 2/2009 |
| JP | 2009-136675 | A | 6/2009 |
| JP | 2010-518900 | A | 6/2010 |
| WO | WO 96/07351 | A1 | 3/1996 |
| WO | WO 97/27802 | A1 | 8/1997 |
| WO | WO 02/094339 | A2 | 11/2002 |
| WO | WO 2004/096022 | A1 | 11/2004 |
| WO | WO 2007/022620 | A2 | 3/2007 |
| WO | WO 2008/100208 | A1 | 8/2008 |
| WO | WO 2008/128350 | A1 | 10/2008 |

OTHER PUBLICATIONS

Samuelsson, U.S. Final Office Action, U.S. Appl. No. 14/000,750, dated May 19, 2016, (9 pgs.).
Canadian Office Action for 2,827,570, EP2012053157, dated Mar. 17, 2015.
Canadian Office Action for 2,816,915, EP2011069728, dated Feb. 3, 2015.
Swedish Office Action and International-Type Search Report dated Aug. 26, 2011, 9 pgs.
Japanese Office Action and English language translation dated May 13, 2014, 7 pgs.
Australian Office Action dated Jul. 2, 2014, 8 pgs.
Japanese Office Action and English language translation dated Aug. 26, 2014, 11 pgs.

(56) References Cited

OTHER PUBLICATIONS

USPTO Notice of Allowance,U.S. Appl. No. 14/000,750, dated Nov. 2, 2016, 11 pages.
USPTO Office Action, U.S. Appl. No. 15/421,651, dated Feb. 23, 2018, 18 pages.
USPTO Office Action, U.S. Appl. No. 15/421,651, dated Oct. 5, 2018, 9 pages.

* cited by examiner

INTERFACE UNIT, MEASUREMENT SYSTEM AND A METHOD IN AN INTERFACE UNIT

FIELD OF THE INVENTION

The present invention relates to an interface unit, a measurement system comprising said interface unit, and a method in an interface unit according to the preamble of the independent claim.

BACKGROUND

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. A blood pressure sensor senses the magnitude of a patient's blood pressure, and converts it into a representative electrical signal that is transmitted to the exterior of the patient.

In the prior art, it is known to mount a sensor at a distal portion of a so-called sensor wire and to position the sensor by using the sensor wire in a blood vessel in a living body to detect a physical parameter, such as pressure or temperature. The sensor includes elements that are directly or indirectly sensitive to the parameter.

One known sensor wire has a typical length of 1.5-2 meter, and comprises a hollow tubing running along a major part of the wire and having an outer diameter in the range of 0.25-0.5 mm, typically approximately 0.35 mm. A core wire is arranged within the tubing and extends along the tubing and often extends out from a distal opening of the tubing. The sensor or sensors is/are preferably arranged in connection with the distal portion of the core wire, e.g. at the distal end of the sensor wire.

The present invention is e.g. applicable in relation with a sensor wire of the type described above.

In one application the sensor wire of the type described above is used to measure pressure in blood vessels, and in particular in the coronary vessels of the heart, e.g. to identify constrictions in the coronary vessels. This may be performed by determining the so-called Fractional Flow Reserve related to the vessel. The sensor wire is typically inserted by use of an insertion catheter, which in turn is inserted via the femoral vein or the radial artery, and guided by the inserted catheter to the measurement site.

In order to power the sensor and to communicate signals representing the measured physiological variable to an external physiology monitor, one or more cables or leads, often denoted microcables, for transmitting the signals are connected to the sensor, and are routed along the sensor wire to be passed out from the vessel to the external physiology monitor, via physical cables or wirelessly.

The sensor element further comprises an electrical circuitry, which generally is connected in a Wheatstone bridge-type of arrangement to one or several piezoresistive elements provided on a membrane. As is well known in the art, a certain pressure exerted on the membrane from the surrounding medium will thereby correspond to a certain stretching or deflection of the membrane and thereby to a certain resistance of the piezoresistive elements mounted thereon and, in turn, to a certain output from the sensor element.

In U.S. 2006/0009817 A1, which is incorporated herein in its entirety, and which is assigned to the present assignee, an example of such a sensor and guide wire assembly is disclosed. The system comprises a sensor arranged to be disposed in the body, a control unit arranged to be disposed outside the body and a wired connection between the sensor and the control unit, to provide a supply voltage from the control unit to the sensor and to communicate a signal there between. The control unit further has a modulator, for modulating the received sensor signal and a communication interface for wireless communication of the modulated signal.

In U.S. Pat. No. 7,724,148 B2, which is incorporated herein in its entirety, and which also is assigned to the present assignee, another example of such pressure measurement system is disclosed. The pressure sensor wire is adapted to be connected, at its proximal end, to a transceiver unit that is adapted to wirelessly communicate via a communication signal with a communication unit arranged in connection with an external device.

In U.S. Pat. No. 6,112,598 A, which is incorporated herein in its entirety, and assigned to the present assignee, and also in U.S. Pat. No. 7,207,227 B2 further examples of such pressure sensors and guide wire assemblies are disclosed.

Thus, the interface unit, the system and the method according to the present invention are applicable in sensor wire assemblies as disclosed in the above-referenced patents and patent application.

Current wireless disposable sensor interface circuitry arranged in connection with such above mentioned transceiver unit, e.g. the Aeris™ (trademark owned by the applicant) transmitter, uses a high-precision matched resistor pair in a bridge type circuit, excited from a voltage source. However, these resistors are costly and can not be readily integrated in a single chip interface circuit.

It is an object of the invention to provide an improved intravascular sensor interface circuit that may be integrated into a single chip configuration and which therefore is less costly, much reduced in physical size and that also provides high measurement accuracy.

SUMMARY OF THE INVENTION

The above-mentioned object is achieved by the present invention according to the independent claim.

Preferred embodiments are set forth in the dependent claims.

According to a first aspect, the present invention relates to an extracorporeale interface unit, for an intravascular measurement system for measuring a physiological, or other, variable in a living body, being adapted to generate a sensor signal in response of a variable. The interface unit comprises a sensor interface circuitry adapted to interface a sensor wire configured to be inserted into the living body and provided with one or many sensor element(s) at its distal region. The sensor interface circuitry further comprises a measurement unit adapted to generate the measured data of the variable as a digital sensor signal. The sensor interface circuitry comprises two current source units CSU1, CSU2, adapted to energize the sensor element(s) via at least two connection points CP1, CP2, . . . CPn, and a switching unit, wherein the switching unit is adapted to alternately switch connection between the current source units and at least two of the connection points using a preset switching frequency having essentially the same connection time period for each connection. The measurement unit is adapted to determine a sensor variable value through a differential voltage $V_{diff}$ related to the variable at two of the connection points CP1, CP2, . . . CPn.

The present invention is based on the insight to use current sources instead of the currently used resistors. Using current sources offer both higher voltage output sensitivity for a given sensor current and can be readily implemented in CMOS for a single-chip interface circuit with much reduced cost and physical size. In order to provide the required high precision for the measurements, i.e. tracking different temperature coefficients that may be present at the two current sources, required for an accurate interface circuit, the temperature drift of the current sources are cancelled by the intravascular sensor interface circuit and the method applied by the unit.

According to a second aspect, the present invention further relates to a measurement system comprising such an extracorporeale interface unit.

According to a third aspect, the present invention relates to a method in an extracorporeale interface unit.

SHORT DESCRIPTION OF THE APPENDED DRAWINGS

DETAILED DESCRIPTION OF PREFERRED EMBODIMENTS OF THE INVENTION

Figure 1:
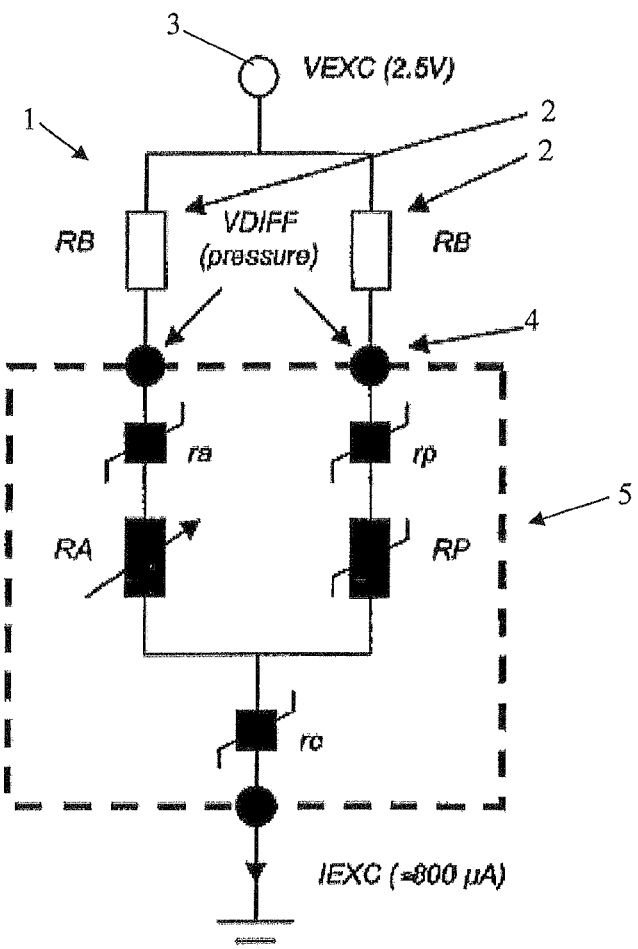
FIG. 1 shows a known sensor interface circuitry using a matched resistor pair.

FIG. 1 shows a known sensor interface circuitry 1 using a matched resistor pair 2 in a Wheatstone bridge-type circuit excited from a constant voltage source 3. The sensor interface circuitry 1 is adapted to be arranged in for example a transceiver unit adapted to be connected, via connection points 4, to the proximal end of a sensor wire 5 (schematically illustrated in FIG. 1) provided, at its distal end, with a sensor to measure a variable in a living body. The Wheatstone bridge-type circuit comprises a matched resistor pair 2 ($R_B$, $R_B$), an active resistor $R_A$ and a passive resistor $R_P$. The sensor element comprises piezoresistive elements mounted on a membrane and is connected to the Wheatstone bridge-type circuit, shown in FIG. 1. When the sensor element is placed in fluid communication within a body cavity, a certain pressure exerted on the membrane from the surrounding medium will correspond to a certain stretching or deflection of the membrane and thereby to a certain resistance of the piezoresistive elements mounted thereon and, in turn, to a certain output from the sensor element.

Figure 2:
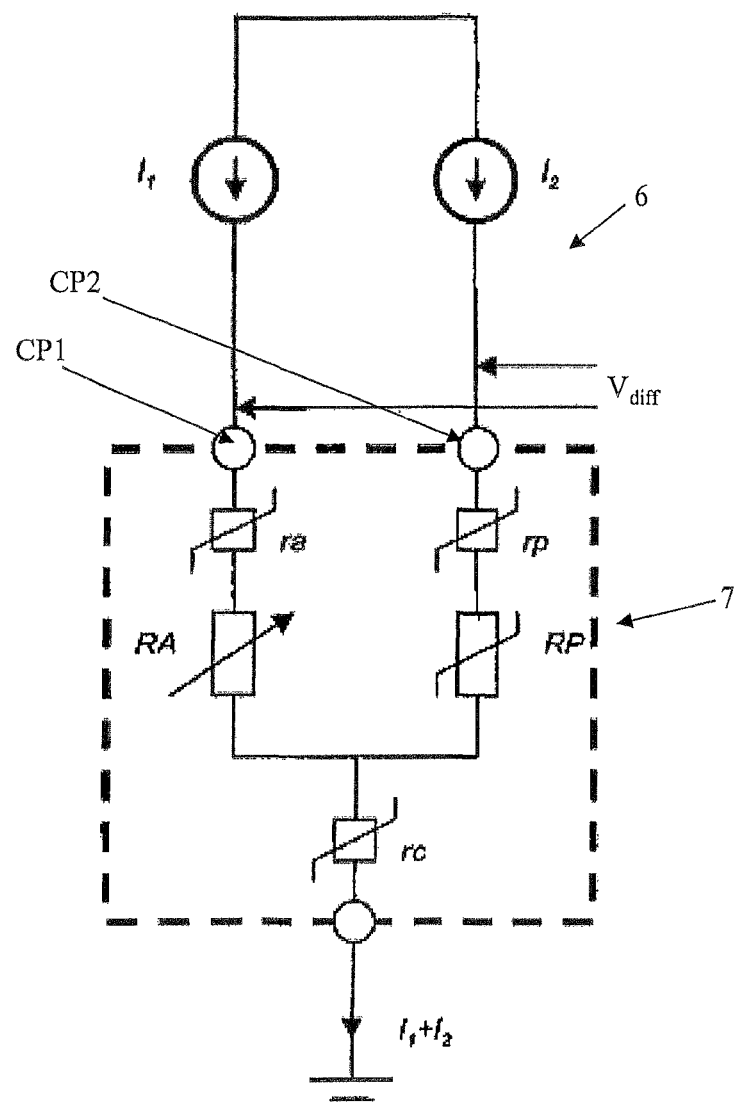
FIG. 2 shows a sensor interface circuitry using current sources.

FIG. 2 illustrates a sensor interface circuitry 6, using two current sources, generating two currents $I_1$, $I_2$, adapted to energize a sensor element (not shown) of a sensor wire 7 via two connection points CP1, CP2.

If $R_A=R_A+ra$, and $R_P=R_P+rp$,
then: $V_{diff}=I_1R_A-I_2R_P$ (since the voltage due to rc cancels)
Introduce a symmetrical offset current of $I_1$ and $I_2$ due to temperature drift:

$I_1=I_1+\Delta I$ $I_2=I_2-\Delta I$

Then: $V_{diff}=R_AI_1R_PI_2+(R_A+R_P)\Delta I$
Thus, in the sensor interface circuitry 6, shown in FIG. 2, $V_{diff}$ is affected by the offset current due to temperature drift ($\Delta I$) of the current sources.

Figure 3:
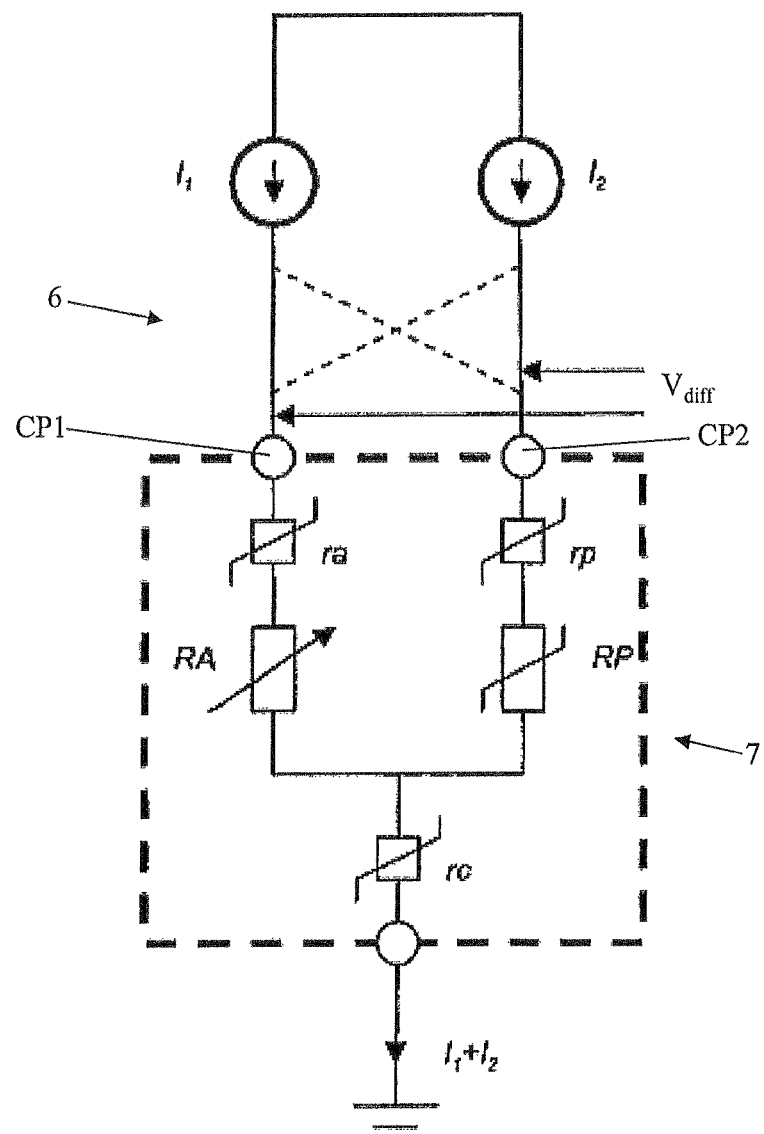
FIG. 3 shows a sensor interface circuitry adapted to be arranged in a interface unit according to the present invention.

FIG. 3 shows a sensor interface circuitry 6 adapted to be arranged in an extracorporeale interface unit, according to a preferred embodiment of the present invention. The sensor interface circuitry 6 is, via at least two connection points CP1, CP2, adapted to be connected to the proximal end of a sensor wire 7 provided, at its distal end, with a sensor to measure a physiological, or other, variable in a living body. The sensor interface circuitry 6 comprises two current sources CSU1, CSU2, generating a first and a second current $I_1$, $I_2$ of which the connections are alternately switched (illustrated by dotted lines, in FIG. 3) between two of the connection points CP1, CP2, such that by taking average readings $V_{diff}$ between the consecutive switching states, the effect of offset currents due to temperature drift is cancelled.

Let $R_A=R_Ara$, and $Rp=Rp+rp$, in the sensor interface circuitry 6 shown in FIG. 3. By using switches, the current sources are alternated between the two branches, The average output voltage between two consecutive connection states is given by:

$$\hat{V}_{diff} = \frac{I_1R_A - I_2R_P + I_2R_A - I_1R_P}{2}$$

which may be rearranged to: $\hat{V}_{diff}=\frac{1}{2}[(R_A-R_P)(I_1+I_2)]$

Introduce a symmetrical offset current of $I_1$ and $I_2$ due to temperature drift:

$I_1=I_1+\Delta I$ $I_2=I_2-\Delta I$

Then: $\hat{V}_{diff}=\frac{1}{2}[(R_A-R_P)(I_1+\Delta I+I_2-I)]$
which reduces to: $\hat{V}_{diff}=\frac{1}{2}[(R_A-R_P)(I_1+I_2)]$
which means that $V_{diff}$ is independent of the offset current temperature drift ($\Delta I$).

Figure 4:
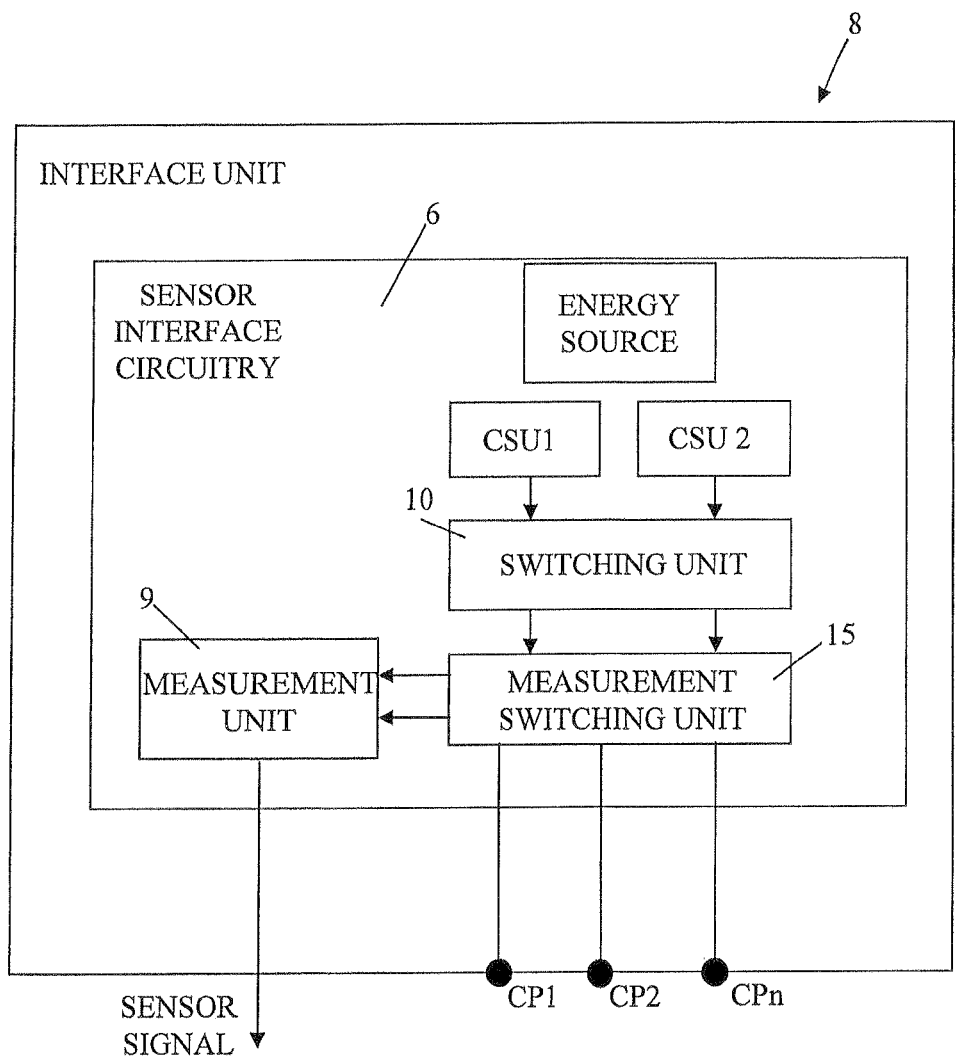
FIG. 4 shows a block diagram schematically illustrating the interface unit according to the present invention.

A block diagram, schematically illustrating the extracorporeale interface unit 8 according to the present invention, is shown in FIG. 4. The extracorporeale interface unit 8, is adapted to generate a digital sensor signal in response of a variable. The interface unit 8 comprises a sensor interface circuitry 6 adapted to interface a sensor wire (not shown) configured to be inserted into the living body and provided with one or many sensor element(s) at its distal region. The sensor interface circuitry 6 further comprises a measurement unit 9 adapted to generate the measured data of the variable as a digital sensor signal. The sensor interface circuitry 6 comprises two current source units CSU1, CSU2, adapted to energize the sensor element(s) via at least two connection points CP1, CP2, . . . CPn, and a switching unit 10, wherein the switching unit 10 is adapted to alternately switch connection between the current source units CSU1, CSU2, and at least two of the connection points CP1, CP2, . . . CPn, using a preset switching frequency having essentially the same connection time period $T_c$ for each connection. The measurement unit 9 is adapted to determine a sensor variable value $V_{diff}$ related to the variable at two of the connection points CP1, CP2, . . . CPn. As seen in FIG. 4, the interface unit 8 also comprises an energy source 11 for energizing the interface unit 8.

According to one embodiment, the measurement unit 9 is adapted to determine a sensor variable value $V_{diff}$ a predetermined time period $T_m$ after the switching being performed.

In one embodiment, the predetermined time period $T_m$ after the switching being performed is less than 10% of the connection time period $T_c$. However, the predetermined time period $T_m$ after the switching being performed may be more than 10% of the connection time period $T_c$. $T_m$ is chosen such that the switching procedure is finalized prior the measurement are initialized.

In a preferred embodiment, the switching unit 10 is a MOSFET switch. However, any other solid state switch or semiconductor device which may be used as a switch may be used.

The sensor variable value $V_{diff}$ is the absolute value of the voltage difference between the connected connection points CP1, CP2, . . . CPn, during one connection time period $T_c$. The variable is determined as a value related to the sensor variable value $V_{diff}$ and the currents generated by the current sources CSU1, CSU2.

In a preferred embodiment, the sensor signal is related to the average value of sensor variable values $V_{diff}$ from at least two connection time periods $T_c$. The connection time periods $T_c$ may be consecutive time periods. Accordingly, $V_{diff}$ may be determined from a number of connection time periods $T_c$ and is given by:

$$\hat{V}_{diff} = \frac{1}{n}\sum_{x=1}^{n}[(R_{Ax} - R_{Px})(I_1 + I_2)]$$

where n preferably is the even number of connection time periods $T_c$ used to calculate $V_{diff}$ during one measurement session.

Let x[i] be the time-discrete digital sensor signal $V_{diff}$. The average signal y[i] can then be created by running x[i] through a moving-average filter given by:

$$\hat{y}[i] = \frac{1}{n}\sum_{j=0}^{n-1}x[i-j]$$

Such an arrangement not only provides the offset current drift cancellation but also acts as a smoothing and low-pass filter to reduce unwanted noise in the digital sensor signal x[i]. The frequency response of such a filter is given by:

$$H[f] = \frac{\sin(\pi f n)}{n \cdot \sin(\pi f)}$$

where f is the relative frequency.

The frequency response and hence the amount of noise reduction can be chosen through selection of the filter length n. Preferably, the value of n is chosen as an even number, typically between 2-128.

A typical sensor response to an applied pressure is given by:

$R_A = R_{A0}(1+PC_{RA}(p-p_0))$ where $R_{A0}$ is the absolute resistance at pressure $p=p_0$, $PC_{RA}$ is the pressure sensitivity of the sensor element, p is the absolute applied pressure and $p_0$ is an absolute reference pressure (typically ambient atmospheric pressure).

Since $V_{diff}$ is a direct representative of $R_A$ it is also a representative of the applied pressure.

According to a preferred embodiment, the switching frequency is approximately 400 Hz which corresponds to a predetermined connection time period $T_c$ of approximately 2.5 ms. However, other switching frequencies within the range 100-1000 Hz may be used.

Figure 5:
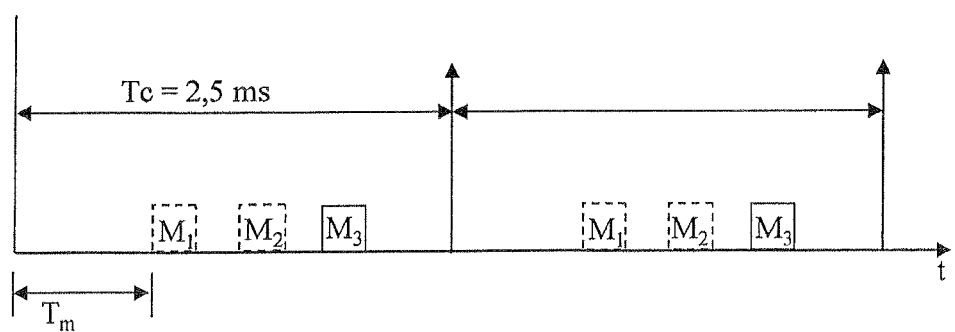
FIG. 5 shows a sampling scheme illustrating two consecutive connection time periods for the interface unit.

The measurement unit 9 is adapted to determine the sensor variable values $V_{diff}$ during a preset part of the connection time period $T_c$ having a predetermined measurement duration, In FIG. 5, a sampling scheme illustrating two consecutive connection time periods $T_c$ for the interface unit, is shown. The connection time period $T_c$ may be divided into a number of measurement periods, where each period may be designated a preset task. For example, if more than one sensor is used, each sensor may be designated a separate measurement period. In the figure, three different measurement periods $M_1$, $M_2$, and $M_3$ are shown. The measurements are performed a predetermined time period $T_m$ after the switching is being performed, where $T_m$ is related to the switching procedure which is discussed above.

The measurements do not need to be performed every connection time period. In some cases it is sufficient to perform the measurement every second, third or fourth connection time period, and even with longer durations between the measurements. This depends naturally of the nature of the variable to be measured. For example, if a temperature is to be measured it is often sufficient to measure at fewer instances compared to the case where pressure is to be measured because the temperature normally changes much slower than the pressure. In FIG. 4, a measurement switching unit 15 adapted to switch connection points CP1, CP2, . . . CPn depending on which variable is to be measured, is shown.

Each one of the current source units CSU1, CSU2 is adapted to generate a current in the range of 100-1000 μA, preferably, approximately 250 μA each. The current source units CSU1, CSU2 are adapted to generate essentially equally large currents.

Figure 6:
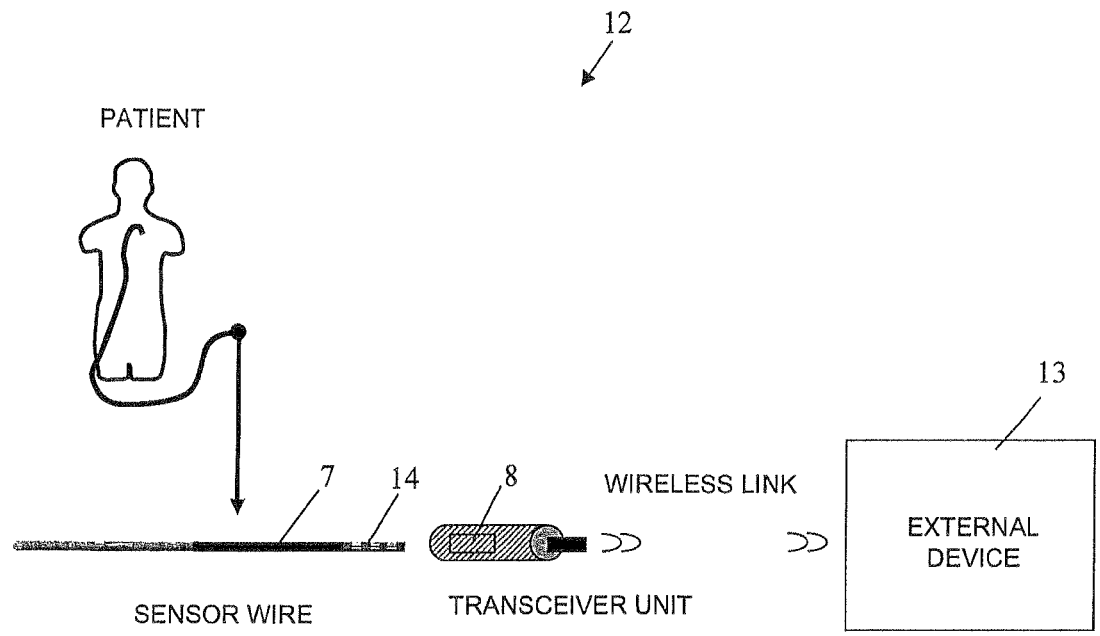
FIG. 6 shows a measurement system, comprising an interface unit arranged in a transceiver unit, according to the present invention.

According to one embodiment, illustrated by FIG. 6, the interface unit is arranged in a transceiver unit 16 adapted to transfer the sensor signal via a wireless connection to an external device 13.

Figure 7:
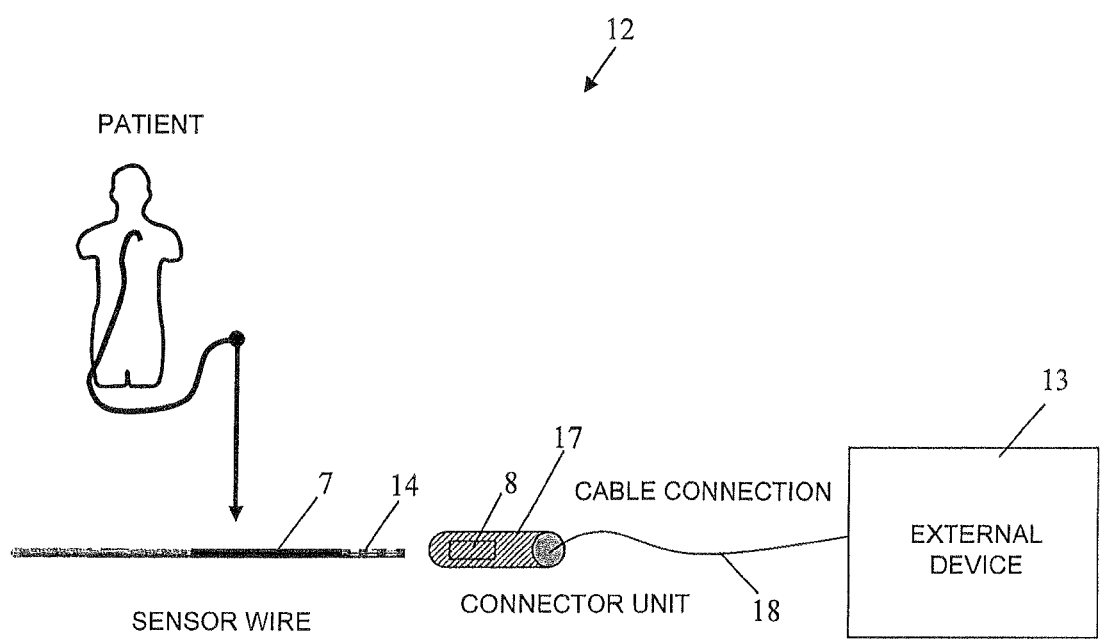
FIG. 7 shows a measurement system, comprising an interface unit arranged in a connector unit, according to the present invention.

In another embodiment, illustrated by FIG. 7, the interface unit 8 is arranged in a connector unit 17 adapted to transfer the sensor signal via a cable connection 18 to an external device 13.

In FIG. 6, a measurement system 12, for intravascular measurements of at least one physiological, or other, variable in a living body, is schematically shown. The measurement system 12 comprises a sensor wire 7, adapted to be inserted into the body, comprising a sensor element (not shown) arranged in a distal region of the sensor wire 7, an external device 13, adapted to receive measured data The measurement system 12 comprises an extracorporale interface unit 8 adapted to be connected to a proximal end 14 of the sensor wire 7. As shown in FIG. 6, the interface unit 8 is adapted to generate a sensor signal in response of a variable, which measured data is transferred to an external device 13. In FIG. 6, the interface unit 8 is arranged in a transceiver unit 16, wherein measured data is transferred by a wireless link. However, and as also mentioned above, the sensor signal may be transferred via a cable connection to the external device 13, as shown in FIG. 7.

Figure 8:
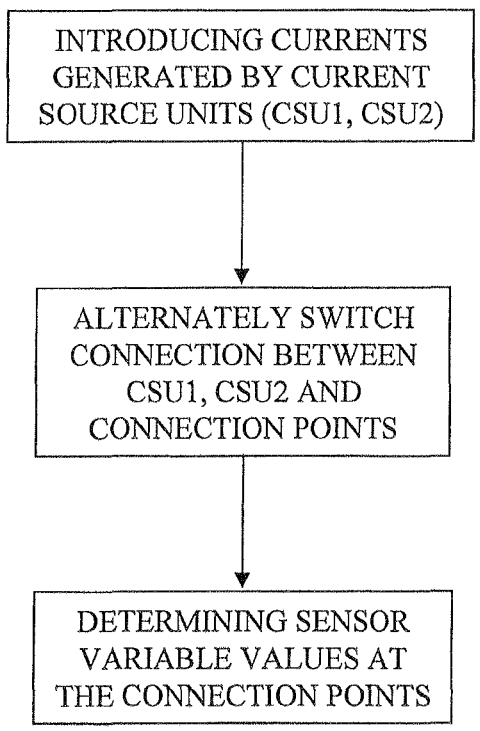
FIG. 8 shows a block diagram schematically illustrating the method in the interface unit.

According to a further aspect, the present invention also relates to a method in an extracorporeale interface unit 8, schematically illustrated in FIG. 8, including:

introducing two currents generated by two current source units CSU1, CSU2 adapted to energize the measurement sensor via at least two connection points CP1, CP2, . . . CPn;

alternately switch connection between the current source units CSU1, CSU2 and the connection points CP1, CP2, . . . CPn, using a preset switching frequency having essentially the same connection time period $T_c$ for each connection;

determining sensor variable values at the connection points CP1, CP2, . . . CPn.

In a preferred embodiment, the method includes:

generating a sensor signal related to the average value of sensor variable values ($V_{diff}$) from at least two connection time periods ($T_c$).

In one embodiment the method includes:

determine said sensor variable value ($V_{diff}$) from the absolute value of the voltage difference between the connected connection points (CP1, CP2, . . . CPn) during one connection time period ($T_c$).

In a further embodiment the method includes:

determine said variable as a value related to the sensor variable value ($V_{diff}$) and the currents generated by said current sources (CSU1, CSU2).

According to one embodiment the method includes:

determine said sensor variable values ($V_{diff}$) during a preset part of said connection time period ($T_c$) having a predetermined measurement duration.

Furthermore, the method may include:

divide said connection time period ($T_c$) into a number of measurement periods, and designate each period a preset task.

According to one embodiment the method includes:

determine said sensor variable value ($V_{diff}$) related to said variable a predetermined time period ($T_m$) after said switching is being performed.

In one embodiment, the method includes:

transferring said sensor signal via a wireless connection to an external device.

According to another embodiment, the method includes:

transferring said sensor signal via a cable connection to an external device.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. An extracorporeal interface unit for an intravascular measurement system for measuring a variable in a living body and generating a sensor signal in response to said variable, the interface unit comprising:
   a sensor interface circuitry configured to interface with a sensor wire that is insertable into the living body and comprises one or more sensor elements at a distal region of the sensor wire, the sensor interface circuitry comprising:
      a measurement unit configured to generate measured data of said variable as a sensor signal;
      two current source units configured to energize said one or more sensor elements via at least two connection points, and
      a switching unit configured to alternately switch connection between said current source units and at least two of said connection points using a preset switching frequency having essentially the same connection time period for each connection,
      wherein said measurement unit is configured to determine a sensor variable value related to said variable based on a measured differential voltage across said at least two connection points.

2. The interface unit according to claim 1, wherein said sensor signal is related to an average value of sensor variable values from at least two connection time periods.

3. The interface unit according to claim 1, wherein said sensor variable value is the absolute value of the differential voltage across the at least two connection points during one connection time period.

4. The interface unit according to claim 1, wherein the variable is determined as a value related to the sensor variable value and the currents generated by said current source units.

5. The interface unit according to claim 1, wherein said switching frequency is approximately 400 Hz.

6. The interface unit according to claim 1, wherein said connection time period is approximately 2.5 ms.

7. The interface unit according to claim 1, wherein said measurement unit is configured to determine said sensor variable value during a preset part of said connection time period having a predetermined measurement duration.

8. The interface unit according to claim 1, wherein said connection time period is divided into a plurality of measurement periods, where each period is designated a preset task.

9. The interface unit according to claim 1, wherein said measurement unit is configured to determine said sensor variable value related to said variable a predetermined time period after said switching is being performed.

10. The interface unit according to claim 9, wherein said predetermined time period after said switching being performed is less than 10% of said connection time period.

11. The interface unit according to claim 1, wherein said switching unit is a MOSFET switch.

12. The interface unit according to claim 1, wherein each one of said current source units is configured to generate a current in the range of 100-1000 µA.

13. The interface unit according to claim 1, wherein said current source units are configured to generate essentially equal currents.

14. The interface unit according to claim 1, wherein said interface unit is arranged in a transceiver unit configured to transfer said sensor signal via a wireless connection to an external device.

15. The interface unit according to claim 1, wherein said interface unit is arranged in a connector unit configured to transfer said sensor signal via a cable connection to an external device.

16. A measurement system for intravascular measurement of at least one variable in a living body, the measurement system comprising:
   a sensor wire that is insertable into the body, and comprises a sensor element arranged at a distal region of said sensor wire;
   an external device configured to receive measured data; and an extracorporeal interface unit according to claim 1, configured to be connected to a proximal end of said sensor wire.

17. A method of using an extracorporeal interface unit according to claim 1, the method comprising:
provide the extracorporeal interface unit of claim 1;
introducing two currents generated by said two current source units to energize a sensor element via the at least two connection points;
alternately switching connection between the current source units and the at least two connection points using a preset switching frequency having essentially the same connection time period for each connection; and
determining the sensor variable value at the at least two connection points.

18. The method according to claim 17, further comprising:
generating the sensor signal related to an average value of sensor variable values from at least two connection time periods.

19. The method according to claim 17, further comprising:
determining said sensor variable value from the absolute value of the differential voltage across the at least two connection points during one connection time period.

20. The method according to claim 17, further comprising:
determining said variable as a value related to the sensor variable value and the currents generated by said current source units.

21. The method according to claim 17, further comprising:
determining said sensor variable values during a preset part of said connection time period having a predetermined measurement duration.

22. The method according to claim 17, further comprising:
dividing said connection time period into a plurality of measurement periods, where each period is designated a preset task.

23. The method according to claim 17, further comprising:
determining said sensor variable value related to said variable a predetermined time period after said switching is being performed.

24. The method according to claim 17, further comprising:
transferring said sensor signal via a wireless connection to an external device.

25. The method according to claim 17, further comprising:
transferring said sensor signal via a cable connection to an external device.

26. The interface unit according to claim 1, wherein the preset switching frequency is in a range of 100 to 1000 Hz.

27. The method according to claim 17, wherein the preset switching frequency is in a range of 100 to 1000 Hz.

* * * * *